United States Patent
Strand

(10) Patent No.: US 6,887,225 B2
(45) Date of Patent: May 3, 2005

(54) SANITARY NAPKIN WITH A CUT-OUT IN THE RELEASE PAPER

(75) Inventor: Lina Strand, Gothenburg (SE)

(73) Assignee: SCA Hygiene Products AB, Gothenburg (CH)

( * ) Notice: Subject to any disclaimer, the term of this patent is extended or adjusted under 35 U.S.C. 154(b) by 314 days.

(21) Appl. No.: 10/149,771

(22) PCT Filed: Dec. 11, 2000

(86) PCT No.: PCT/SE00/02484
§ 371 (c)(1),
(2), (4) Date: Jun. 13, 2002

(87) PCT Pub. No.: WO01/41692
PCT Pub. Date: Jun. 14, 2001

(65) Prior Publication Data
US 2002/0183708 A1 Dec. 5, 2002

(30) Foreign Application Priority Data
Dec. 13, 1999 (SE) .............................................. 9904547

(51) Int. Cl.$^7$ ............................................. A61F 13/15
(52) U.S. Cl. ........................... 604/385.05; 604/385.03; 604/385.01; 604/386; 604/387
(58) Field of Search ....................... 604/385.05, 385.03, 604/385.04, 386, 387, 385.01

(56) References Cited

U.S. PATENT DOCUMENTS

| | | | | |
|---|---|---|---|---|
| 4,605,404 A | * | 8/1986 | Sneider | 604/385.05 |
| 4,690,680 A | * | 9/1987 | Higgins | 604/386 |
| 5,037,418 A | * | 8/1991 | Kons et al. | 604/387 |
| 5,127,911 A | | 7/1992 | Baharav | |
| 5,681,303 A | * | 10/1997 | Mills et al. | 604/385.26 |

FOREIGN PATENT DOCUMENTS

| | | |
|---|---|---|
| EP | 0 681 819 A1 | 11/1995 |
| WO | WO 98/20823 | 5/1998 |

* cited by examiner

Primary Examiner—Jacqueline F. Stephens
(74) Attorney, Agent, or Firm—Young & Thompson

(57) ABSTRACT

An absorbent article in the form of a sanitary napkin (1), a panty liner or an incontinence protector for women, comprises an absorbent body (2) and a liquid-impervious casing sheet (4) that covers one side of the absorbent body and is joined thereto, either directly or indirectly, wherein the liquid-impervious casing sheet is coated with an adhesive layer (5) that extends at least over a part of the casing sheet, and a removable protective sheet (6) covering the adhesive layer. The protective layer (6) includes a cut-out (7) that extends symmetrically on respective sides of the longitudinal symmetry axis (A—A) of the article, and at least one piece of material (8) that extends in the cut-out.

19 Claims, 2 Drawing Sheets

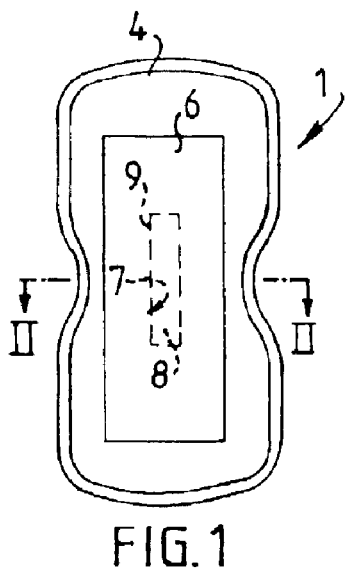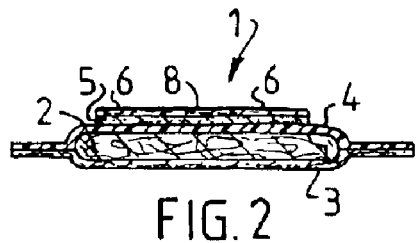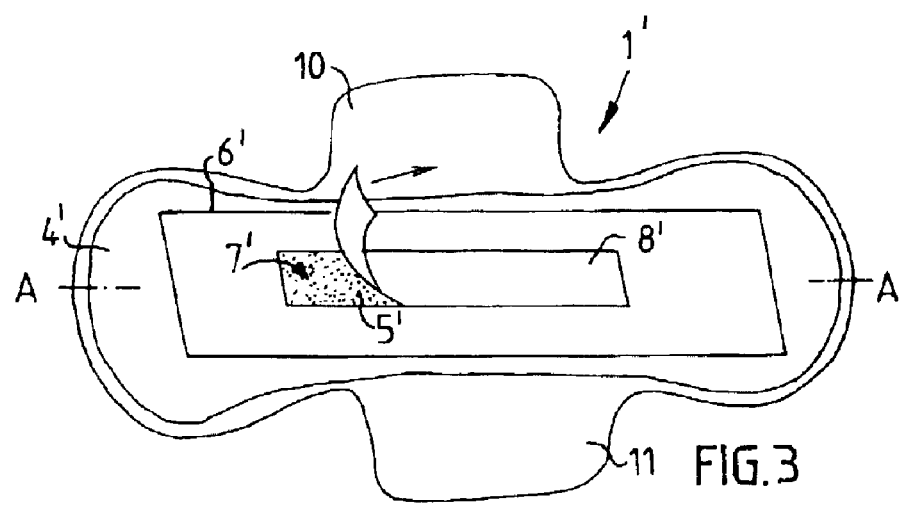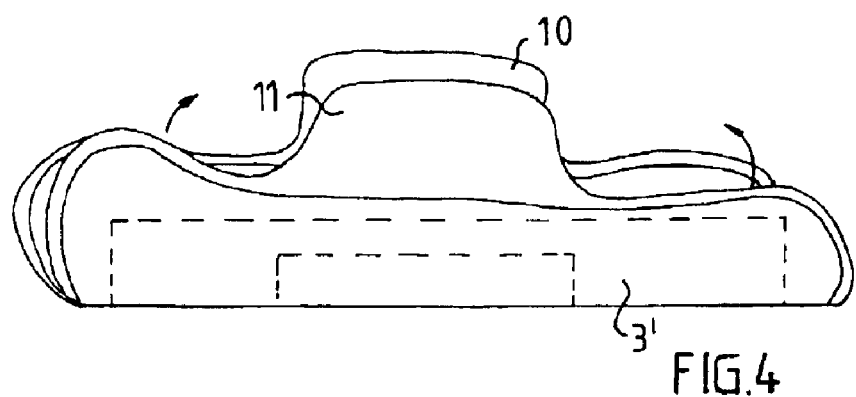

SANITARY NAPKIN WITH A CUT-OUT IN THE RELEASE PAPER

This is the 35 USC 371 national stage of International Application PCT/SE00/02484 filed on Dec. 11, 2000, which designated the United States of America.

FIELD OF INVENTION

The present invention relates to an absorbent article in the form of a sanitary napkin, a panty liner or an incontinence protector for women, comprising an absorbent body and a liquid-impervious outer sheet or top sheet that covers one side of the absorbent body and is connected thereto, either directly or indirectly, said liquid-impervious outer sheet being coated with an adhesive layer that extends at least over a central part of said sheet, and a removable protective layer that covers the adhesive layer.

DESCRIPTION OF THE BACKGROUND ART

One reason why absorbent articles of the aforementioned kind tend to leak when in use is because they do not lie against the wearer's body, therewith allowing liquid to run on the surface of the article and beyond the edges of said article without being absorbed. In order to resolve this problem, it is not unusual to provide the article with a central upstanding part which comes into positive contact with the user's body when the article is donned. It is also known to provide sanitary napkins and corresponding articles with upstanding parts that ensure that a donned article will not be moved laterally by those forces to which it is subjected in use.

One drawback with absorbent articles that include such outwardly projecting parts is that they complicate packaging of the articles. The articles are often packaged one on top of the other and give the packages a large volume, which increases the transport costs and storage costs of the articles. There is also a risk that the outwardly projecting parts will be deformed during transportation and storage. Some users also experience articles that include outwardly projecting parts uncomfortable and unpleasant to wear. EP-A1-0 681 819 teaches an absorbent article that solves the aforesaid problems by means of an upstanding part that is formed by the wearer immediately prior to donning the article. This known article includes several adhesive strings which are each protected by release paper The application of a plurality of adhesive strings complicates the manufacture of such articles, particularly when it is necessary to provide each of the strings with release paper.

Furthermore, handling of such articles is complicated by the need to remove several release papers in a specific order, when the wearer avails herself of the possibility of shaping the article to obtain an upstanding part.

An object of the present invention is to provide an article of the aforesaid kind which solves the aforesaid problems in principle in the same fashion as with the article known from the aforesaid patent publication, but without complicating the manufacture and use of the article.

SUMMARY OF THE INVENTION

These objects are achieved with an absorbent article in the form of a sanitary napkin, a panty liner or an incontinence napkin for women that comprises an absorbent body and a liquid-impervious casing sheet or backing sheet that covers one side of the absorbent body and is connected thereto either directly or indirectly, said liquid-impervious casing sheet being coated with an adhesive layer that extends at least over a central part of the casing sheet, and a removable protective layer that covers said adhesive layer, wherein said article is characterised in that the protective layer includes a cut-out or recess that extends symmetrically on respective sides of the longitudinal symmetry axis of the article, and at least one piece of material that extends into the cut-out. Because the liquid-impervious casing sheet is only coated with one single adhesive layer, manufacture of the article is simplified significantly in relation to articles to which several strings of adhesive are applied. Furthermore, the article design enables the adhesive layer to be covered with one single release paper or corresponding device, and that the cut-out and the piece of material located therein can be applied in one single manufacturing stage. The application of adhesive and protective layer is thus very easy to achieve. Handling of the article is also easy and uncomplicated since only one single component needs to be removed from the adhesive coating in order to enable the article to be fastened to a pair of panties or a pair of underpants.

In one preferred embodiment, one single piece of material extends into the cut-out, said piece having the same dimensions as the cut-out and consisting of the same material as the remainder of the protective layer. This piece of material may conveniently consist of the part that was cut from the protective layer in providing the cut-out or recess and is conveniently joined to the protective layer by at least one narrow tongue.

In another embodiment, three pieces of material extend into the cut-out, a first piece that extends symmetrically on respective sides of the longitudinal symmetry axis of the article, and two pieces that are located on respective sides of the first piece of material and that have the same dimensions, wherewith the three pieces of material together cover the cutout in the protective layer.

The cut-out is conveniently situated closer to the front end of the article than to its rear end in both of the aforesaid embodiments, and the protective layer is comprised of release paper. The absorbent body is preferably comprised of cellulose fluff and is enclosed between an inner liquid-pervious outer sheet or top sheet and said liquid-impervious casing sheet or backing sheet. The absorbent body will preferably have a thickness of less than 15 mm. The adhesive layer may comprise a pressure-sensitive hotmelt glue.

BRIEF DESCRIPTION OF THE DRAWINGS

The present invention will now be described with reference to the accompanying drawings, in which FIG. 1 is a schematic plan view of a sanitary napkin according to a first embodiment of the invention with the liquid-impervious sheet facing towards the viewer;

FIG. 2 is a cross-sectional view taken on the line II—II in FIG. 1;

FIGS. 3–5 illustrate schematically the various steps taken in forming a ridge-like, outwardly projecting part of a sanitary napkin according to a second embodiment of the invention;

DESCRIPTION OF PREFERRED EMBODIMENTS

Figure 5:
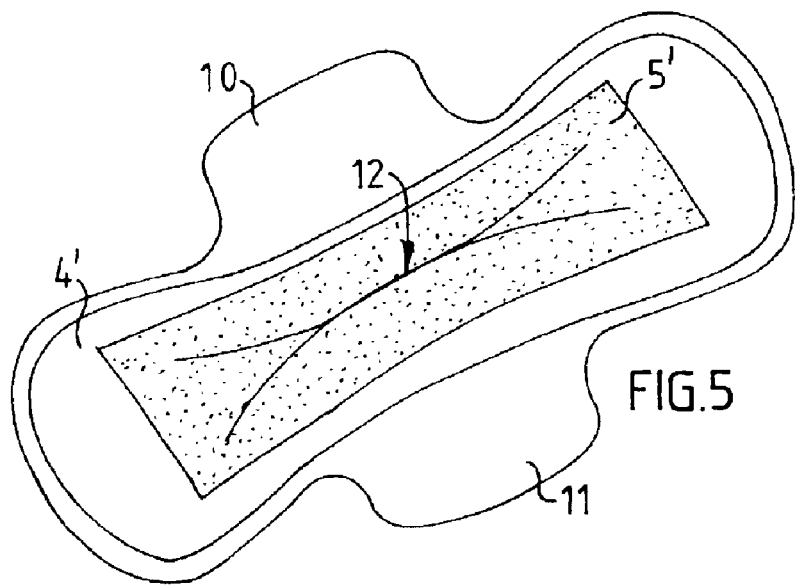

FIGS. 1–2 illustrate schematically a first embodiment of an inventive sanitary napkin 1. The napkin 1 includes an absorbent body 2 enclosed between a liquid-pervious, inner casing sheet or top sheet 3 and a liquid-impervious outer casing sheet or backing sheet 4. The casing sheets 3 and 4 extend beyond the absorbent body 2 and are mutually joined at those parts which lie beyond the absorbent body. An adhesive layer 5 extends over a large part of the liquid-impervious sheet 4, so as to enable the napkin to be fastened to a pair of panties. The adhesive layer is covered by a protective layer 6. The protective layer 6 includes a rectangular cut-out 7 in which there is disposed a piece of material 8. The cutout 7 extends symmetrically on respective sides of the longitudinal symmetry axis of the napkin. The piece of material 8 of the FIG. 1 embodiment is joined to the protective layer 6 via four narrow tongues 9.

In the illustrated embodiment, the piece of material 8 and the tongues 9 are obtained by forming the cut-out 7 in the protective layer 6. This facilitates manufacture of the sanitary napkin 1, by virtue of the fact that the protective layer 6 and the piece of material 8 can be applied to the adhesive layer as one single component. Naturally, it is also possible to cutout the piece of material 8 completely from the protective layer 6 and to apply this piece of material as a separate component. It is also possible to allow the piece of material to consist of material different to the protective layer, although this is not preferred Alternatively, the cut-out 7 and the piece of material 8 can be formed subsequent to having applied the protective layer 6 to the adhesive layer 8, e.g. by milling-out the cut-out or recess 7. The protective layer and adhesive layer can therefore be applied extremely easily from a manufacturing/technical aspect in the case of an inventive absorbent article.

The absorbent body 2 is preferably comprised of cellulose fluff mass that has been compressed to a density of 0.1–0.5 g/cm$^3$ and to a thickness smaller than 15 mm. Other natural absorbent fibres, such as cotton fibres or peat mass can be used, as can also synthetic fibres or a mixture of synthetic fibres and natural fibres. It is also conceivable to admix a superabsorbent material. In the case of the described embodiment, the absorbent body consists of one single layer, although it may, of course, be a multi-layer absorbent body. The absorbent body may also include a shape-stabilising and/or liquid-dispersing layer or devices, such as a binder for holding short fibres and particles in a coherent unit form. The absorbent body may also be sufficiently flexible to enable said body to be folded without losing a large quantity of fibres.

The liquid-pervious sheet 3 is preferably comprised of nonwoven material, e.g. a spunbond material of cellulose or cotton fibres. Also conceivable is the use of synthetic fibres, such as fibres of polyethylene, polypropylene, polyurethane, polyester, nylon or regenerated cellulose. The sheet 3 may also be comprised of a perforated plastic film, a plastic net or a laminate of one such sheet and a nonwoven sheet. All materials that are used to produce the top sheets of absorbent articles can be used for the sheet 3.

The liquid-impervious casing sheet 4 is comprised of a flexible material, preferably a thin film of polyethylene, polypropylene or polyester, although it may also consist of a laminate of one such film and one nonwoven layer. All materials that are used as liquid-impervious backing sheets in absorbent articles can be used in the present context.

The adhesive layer 5 is comprised of an adhesive that is suitable for removably fastening the napkin to the inside of a pair of panties. The adhesive is conveniently comprised of a pressure-sensitive hotmelt glue e.g. ECOMELT H745 from Collano, Switzerland. Other types of adhesive may alternatively be used, such as acrylate glue.

The protective layer 6, and therewith also the piece of material 8, will preferably consist of release paper, i.e. silicone coated paper. Alternatively, there may be used other materials that adhere to the adhesive layer 6 with a smaller adhesive force than the force at which the layer 6 adheres to the liquid-impervious casing sheet 4 and which can be peeled off the layer 6 without reducing the adhesive force of the then exposed sheet 5. An example of such material is ESP 48, Lohjan Paperi OY, Finland.

FIGS. 3–5 illustrate schematically a second embodiment of an inventive sanitary napkin 1'. This napkin differs from the napkin 1 shown in FIGS. 1 and 2. The main difference is that the piece of material 8' is comprised of a piece that has been separated from the remainder of the protective layer 6', and that the casing sheets 3', 4' form so-called wings 10, 11 in the central part of the napkin. Those components of the sanitary napkin 1' that find correspondence in the components of the sanitary napkin 1 have been identified with the same reference signs to which a prime has been added.

As before mentioned, one probable reason for leakage in respect of absorbent articles of the aforedescribed kind is because the article does not lie in abutment with the wearer's body in use, therewith allowing liquid to run on the surface of the article and outwardly of the edges thereof without being absorbed. It is not unusual for this problem to be resolved by providing the article with a central upstanding part which ensures contact with the user's genitals when donning the article. FIGS. 3–5 illustrate schematically how such a ridge-like part can be formed readily with an inventive sanitary napkin.

Such a ridge-like part is formed, by first pulling away the piece of material 8', so as to expose the adhesive layer 5' in the cut-out 7' in the protective layer 6'. FIG. 3 shows the napkin 1' with the piece of material 8' partially pulled away.

After having pulled the piece of material 8' away from the napkin 1', the napkin is folded about its longitudinal symmetry axis A—A, therewith bringing those parts of the liquid-pervious sheet 4' that lie on respective sides of the longitudinal symmetry axis into abutment with each other, and then clamping together the folded napkin within the region of the cut-out 7', thereby joining together the mutually facing sides of the folded napkin within said region of the cut-out 7'. FIG. 4 shows the napkin in its folded state. The sides of the folded napkin are then folded back, so that the underside of the napkin, i.e. the side to be fastened to the inside of a pair of panties, is returned to a generally flat state, whereafter the protective layer 6' is removed and the napkin is placed in position in the wearer's panties. When the sides of the napkin are refolded, those parts of the folded napkin fastened within the region of said cut-out will remain folded, so that a pleat 12 whose height corresponds to half the width of the cut-out will remain after the napkin has been refolded.

Figure 6:
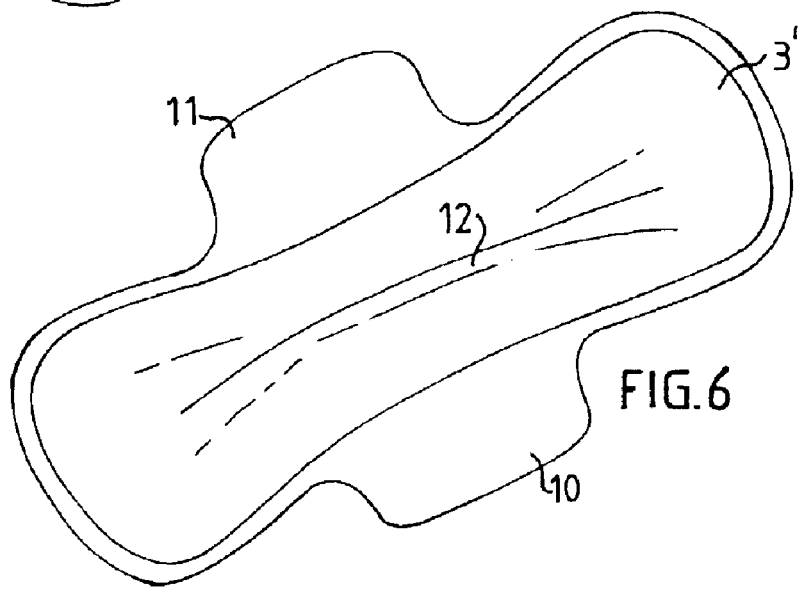
FIG. 6 is a view similar to that of FIG. 5, but with the liquid-pervious sheet of the napkin facing towards the viewer.

FIGS. 5 and 6 show the sanitary napkin 1' with the protective layer 6' removed, before placing the napkin in position in the wearer's panties with the liquid-pervious and liquid-impervious sheets facing towards the viewer. As will best be seen from FIG. 6, the napkin includes a ridge-part 12 which projects out from that side of the napkin 1' which lies proximal to the wearer's body in use, said part 12 having been formed by folding and refolding the napkin. The height of the ridge-like part within the region of the cut-out 7' corresponds to half the width of the cut-out 7' and its width corresponds to twice the thickness of the napkin 1'. The height of the ridge-like part 12 decreases in the longitudinal direction from the region of the cut-out and towards each end of said napkin, whereas the width of said ridge-like part increases.

If the user of the napkin shown in FIG. 3 wishes to use the napkin without forming a ridge-like part, the napkin can be placed in position in the wearer's panties immediately after having removed the protective layer 6'. It will be noted that in respect of this latter use, it is not necessary to remove the piece of material 8', since those parts of the adhesive layer 5' that are exposed when removing the parts of the protective layer that lie outwardly of the piece of material 8' have a sufficiently large surface area to ensure firm attachment of the napkin to the wearer's panties.

The sanitary napkin 1 shown in FIGS. 1 and 2 can be provided with a ridge-like part in a manner similar to that described with respect to the napkin 1'. In this regard, it is pointed out that the tongues 9 will, of course, be sufficiently narrow so as to break easily when pulling-off the piece of material 8, so that said piece can be pulled away from the adhesive layer 5 without being accompanied by the remainder of the protective layer 6.

Figure 7:
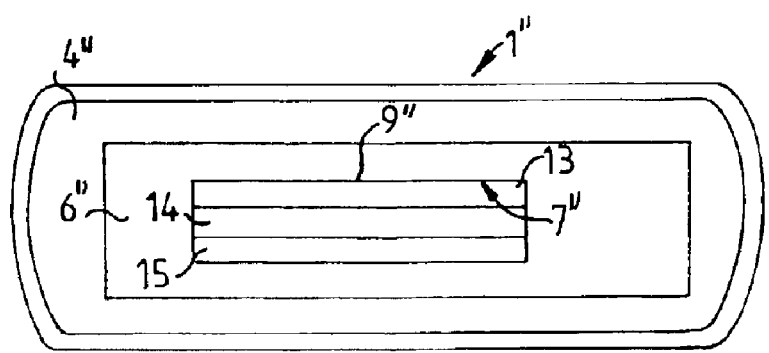
FIG. 7 illustrates a third embodiment of an inventive sanitary napkin.

FIG. 7 illustrates a further embodiment of an inventive sanitary napkin, here referenced 1". The primary difference between this napkin embodiment and the embodiment illustrated in FIGS. 1 and 2 is that the napkin shown in FIG. 7 has a generally rectangular shape instead of the hourglass shape of the napkin 1 shown in FIGS. 1 and 2, and in that said napkin includes three pieces of material 13, 14, 15 disposed in the cut-out 7" instead of only one piece of material 8. Those components of the napkin 1" that find correspondence in the napkin 1 have been identified by the same reference signs with the addition of a double prime. The pieces of material 13 and 15 have mutually the same dimensions and extend equidistantly from the longitudinal symmetry line of the napkin 1".

The sanitary napkin 7" can be provided with a ridge-like part essentially in the same manner as that described with respect to napkins 1 and 1'. The sole difference is that the piece of material 14 is left in the cut-out 7" subsequent to having removed the pieces of material 13 and 15. With respect to the ridge-like part that is then formed, the uppermost part of the pleat formed when those parts of the cut-out 7", which is exposed when removing the pieces of material 13 and 15, are fastened together when folding the napkin 7", which constitutes a stage in the formation of the ridge-like part and is illustrated in respect of the napkin 7' in FIG. 4, has sides which are not joined together. This means that the uppermost part of the pleat will be less stiff than if the sides were fastened together. The upper part of a ridge-like part formed in the napkin 7" can therewith be easily deformed and adapted to the body contours of the wearer.

It will be understood that the described embodiments can be modified within the scope of the invention, particularly with respect to the design of the napkin and the choice of material. For instance, the liquid-pervious sheet may be omitted if the absorbent body has sufficient mechanical strength and softness in both a dry and wet state to permit such omission. As before mentioned, the invention can also be applied in respect of panty liners and incontinence napkins for women. Moreover, an inventive absorbent article can be provided with ridge-like parts that extend in regions of the article other than central regions. For instance, the article can be provided with a ridge-like part that extends over that part of the article which extends rearwards in use, by positioning the cut-out at an appropriate distance from the rear end of the article. The invention is therefore solely limited by the contents of the accompanying Claims.

What is claimed is:

1. An absorbent article in the form of a sanitary napkin, a panty liner or an incontinence protector for women, comprising:
    an absorbent body and a liquid-impervious casing sheet that covers one side of the absorbent body and is joined thereto, either directly or indirectly;
    said liquid-impervious casing sheet being coated with a continuous adhesive layer that extends at least over a central part of the casing sheet; and
    a removable protective layer covering the adhesive layer; said protective layer including a cut-out which extends symmetrically on respective sides of the longitudinal symmetry axis of said article, and at least one piece of material that extends in and covers entirely said cut-out.

2. The article according to claim 1, wherein one single piece of material extends in the cut-out; said single piece of material having the same dimensions as the cut-out and consisting of the same material as the protective layer.

3. The article according to claim 2, wherein said piece of material consists of the part removed from the protective layer in forming the cut-out.

4. The article according to claim 3, wherein the piece of material removed from the protective layer is joined to said protective layer by at least one narrow tongue.

5. The article according to claim 1, wherein three pieces of material extend in the cut-out, a first piece which extends symmetrically on respective sides of the longitudinal symmetry axis of the article, and two second pieces that are located on respective sides of the first piece of material and have the same dimensions; said three pieces of material together covering the cut-out in the protective layer.

6. The article according to claim 1, wherein the cut-out is located closer to the front end of the article than to its rear end.

7. The article according to claim 1, wherein the protective layer is comprised of release paper.

8. The article according to claim 1, wherein the absorbent body comprises cellulose fluff and is enclosed between an inner, liquid-pervious casing sheet and said liquid-impervious casing sheet.

9. The article according to claim 1, wherein the absorbent body has a thickness of less than 15 mm.

10. The article according to claim 1, wherein the adhesive layer comprises a pressure-sensitive hotmelt glue.

11. An absorbent article in the form of a sanitary napkin, a panty liner or an incontinence protector for women, comprising:
    an absorbent body and a liquid-impervious casing sheet that covers one side of the absorbent body and is joined thereto, either directly or indirectly;
    said liquid-impervious casing sheet being coated with an adhesive layer that extends at least over a central part of the casing sheet; and
    a removable protective layer covering the adhesive layer; said protective layer including a cut-out which extends symmetrically on respective sides of the longitudinal symmetry axis of said article, and one single piece of material that extends in said cut-out; said single piece of material having the same dimensions as the cut-out and consisting of the same material as the protective layer.

12. The article according to claim 11, wherein said piece of material consists of the part removed from the protective layer in forming the cut-out.

13. The article according to claim 12, wherein the piece of material removed from the protective layer is joined to said protective layer by at least one narrow tongue.

14. The article according to claim 11, wherein three pieces of material extend in the cut-out, a first piece which extends symmetrically on respective sides of the longitudinal symmetry axis of the article, and two second pieces that are located on respective sides of the first piece of material and have the same dimensions; said three pieces of material together covering the cut-out in the protective layer.

15. The article according to claim 11, wherein the cut-out is located closer to the front end of the article than to its rear end.

16. The article according to claim 11, wherein the protective layer is comprised of release paper.

17. The article according to claim 11, wherein the absorbent body comprises cellulose fluff and is enclosed between an inner, liquid-pervious casing sheet and said liquid-impervious casing sheet.

18. The article according to claim 11, wherein the absorbent body has a thickness of less than 15 mm.

19. An absorbent article in the form of a sanitary napkin, a panty liner or an incontinence protector for women, comprising:

an absorbent body and a liquid-impervious casing sheet that covers one side of the absorbent body and is joined thereto, either directly or indirectly;

said liquid-impervious casing sheet being coated with an adhesive layer that extends at least over a central part of the casing sheet; and a removable protective layer covering the adhesive layer; said protective layer including a cut-out which extends symmetrically on respective sides of the longitudinal symmetry axis of said article, and which is located closer to the front end of the article than to its rear end; said protective layer including at least one piece of material which extends in said cut-out.

* * * * *